(12) United States Patent
Sullivan et al.

(10) Patent No.: US 10,667,923 B2
(45) Date of Patent: Jun. 2, 2020

(54) SACRO-ILIAC JOINT IMPLANT SYSTEM AND METHOD

(71) Applicant: Warsaw Orthopedic, Inc, Warsaw, IN (US)

(72) Inventors: Charles S. Sullivan, Germantown, TN (US); Jaredan Braal, Memphis, TN (US); Gregory C. Marik, Collierville, TN (US); Newton H. Metcalf, Jr., Memphis, TN (US); Domagoj Coric, Charlotte, NC (US); Alexander Vaccaro, Gladwyne, PA (US); Hugo Benalcazar, Phoenix, MD (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/339,861

(22) Filed: Oct. 31, 2016

(65) Prior Publication Data

US 2018/0116814 A1    May 3, 2018

(51) Int. Cl.
*A61B 17/70*   (2006.01)
*A61F 2/44*    (2006.01)
(Continued)

(52) U.S. Cl.
CPC .......... *A61F 2/446* (2013.01); *A61B 17/7055* (2013.01); *A61B 17/864* (2013.01);
(Continued)

(58) Field of Classification Search
CPC ............ A61B 17/7064; A61B 17/7098; A61B 17/8625; A61B 17/864; A61B 17/8605; A61B 17/0642; A61B 17/7055; A61B 17/7044; A61B 17/8685; A61B 17/8695; A61F 2/30988; A61F 2/4455; A61F 2002/30032; A61F 2002/30062; A61F 2002/30092; A61F 2002/30289; A61F 2002/30354; A61F 2002/30405; A61F 2002/30509; A61F 2002/3055; A61F 2002/30772; A61F 2002/30784; A61F 2002/3085; A61F 2002/3093;
(Continued)

(56) References Cited

U.S. PATENT DOCUMENTS 4,423,721 A   1/1984   Otte et al.
4,612,918 A   9/1986   Slocum
(Continued)

FOREIGN PATENT DOCUMENTS

WO   2015118543 A1   8/2015
WO   2015162612 A1   10/2015
WO   2016065489 A1   5/2016

OTHER PUBLICATIONS

European Application No. 17195856.4, European Search Report dated Mar. 19, 2018 from European Patent Office (EPO) 80298 Munich, Germany.

*Primary Examiner* — Pedro Philogene (57) ABSTRACT

A sacro-iliac implant includes a body having a proximal portion and a distal tip. The proximal portion includes an inner surface and a uniform diameter. The inner surface includes a first mating surface engageable with a first instrument surface and a second mating surface engageable with a second instrument surface. Systems, constructs, instruments and methods are disclosed.

20 Claims, 8 Drawing Sheets

(51) Int. Cl.
*A61F 2/46* (2006.01)
*A61B 17/86* (2006.01)
*A61F 2/30* (2006.01)
*A61F 2/28* (2006.01)

(52) U.S. Cl.
CPC ........ *A61B 17/8645* (2013.01); *A61F 2/4611* (2013.01); *A61F 2002/2835* (2013.01); *A61F 2002/30622* (2013.01); *A61F 2002/30995* (2013.01)

(58) Field of Classification Search
CPC .. A61F 2002/30995; A61F 2002/30677; A61F 2310/00023; A61F 2310/00029; A61F 2310/00179; A61F 2310/00293; A61F 2310/00359; A61F 2310/00011; A61F 2310/00796
USPC ................. 606/300–328; 623/17.11–17.16
See application file for complete search history.

(56) References Cited

U.S. PATENT DOCUMENTS

| | | | |
|---|---|---|---|
| 4,773,402 | A | 9/1988 | Asher et al. |
| 4,961,740 | A | 10/1990 | Ray et al. |
| 5,026,373 | A | 6/1991 | Ray et al. |
| 5,108,397 | A | 4/1992 | White |
| 5,334,205 | A | 8/1994 | Cain |
| 5,669,909 | A | 9/1997 | Zdeblick et al. |
| 5,827,285 | A * | 10/1998 | Bramlet ............ A61B 17/68 606/60 |
| 5,964,768 | A * | 10/1999 | Huebner ........... A61B 17/1686 411/115 |
| 6,021,343 | A * | 2/2000 | Foley .................... A61B 17/16 600/417 |
| 6,030,162 | A | 2/2000 | Huebner |
| 6,053,916 | A * | 4/2000 | Moore ................ A61F 2/30988 606/86 R |
| 6,217,331 | B1 | 4/2001 | Rogers et al. |
| 6,224,603 | B1 | 5/2001 | Marino |
| 6,299,615 | B1 | 10/2001 | Huebner |
| 6,635,059 | B2 | 10/2003 | Randall et al. |
| 6,648,903 | B1 | 11/2003 | Pierson, III |
| D484,596 | S | 12/2003 | Ryan et al. |
| 6,755,835 | B2 | 6/2004 | Schultheiss et al. |
| 6,964,665 | B2 | 11/2005 | Thomas et al. |
| 6,981,974 | B2 | 1/2006 | Berger |
| 7,338,286 | B2 | 3/2008 | Porter et al. |
| 7,354,442 | B2 | 4/2008 | Sasso et al. |
| D574,495 | S | 8/2008 | Petersen |
| 7,473,256 | B2 * | 1/2009 | Assell ................ A61B 17/025 606/90 |
| 7,491,236 | B2 * | 2/2009 | Cragg ................ A61B 17/70 623/17.11 |
| 7,527,611 | B2 | 5/2009 | Sweeney |
| 7,575,572 | B2 | 8/2009 | Sweeney |
| 7,582,107 | B2 | 9/2009 | Trail et al. |
| 7,597,557 | B2 | 10/2009 | Fromovich et al. |
| 7,625,395 | B2 | 12/2009 | Muckter |
| 7,637,954 | B2 | 12/2009 | Michelson |
| 7,648,509 | B2 | 1/2010 | Stark |
| 7,766,917 | B2 | 8/2010 | Kugler et al. |
| 7,806,693 | B2 | 10/2010 | Hurson |
| 7,827,694 | B2 | 11/2010 | Soler et al. |
| 7,845,945 | B2 | 12/2010 | Canter |
| 7,862,587 | B2 | 1/2011 | Jackson |
| 7,905,908 | B2 | 3/2011 | Cragg et al. |
| 7,938,836 | B2 * | 5/2011 | Ainsworth ........... A61B 17/025 606/99 |
| D643,921 | S | 8/2011 | Davila |
| 8,038,442 | B2 | 10/2011 | Hurson |
| 8,167,947 | B2 * | 5/2012 | Ainsworth ............ A61B 17/70 623/17.11 |
| 8,394,108 | B2 | 3/2013 | McLean et al. |
| 8,394,132 | B2 | 3/2013 | Lewis et al. |
| 8,460,307 | B2 | 6/2013 | Saidha et al. |
| 8,574,273 | B2 | 11/2013 | Russell et al. |
| D696,466 | S | 12/2013 | Silva |
| D700,322 | S | 2/2014 | Kleiner |
| 8,747,472 | B2 | 6/2014 | Ainsworth et al. |
| 8,758,012 | B2 | 6/2014 | Hurson |
| 8,784,431 | B1 | 7/2014 | Harder et al. |
| 8,932,059 | B2 | 1/2015 | Dukhan |
| 8,932,303 | B2 | 1/2015 | Bouliane |
| 8,968,372 | B2 | 3/2015 | Biedermann et al. |
| 8,974,932 | B2 | 3/2015 | McGahan et al. |
| 8,986,348 | B2 | 3/2015 | Reiley |
| 9,095,397 | B2 | 8/2015 | Kremer et al. |
| 9,113,972 | B2 | 8/2015 | Trudeau |
| 9,119,685 | B2 | 9/2015 | Butler et al. |
| 9,161,799 | B2 * | 10/2015 | Benson ............ A61B 17/1655 |
| 9,173,042 | B2 | 10/2015 | Jinton et al. |
| 9,364,299 | B2 | 6/2016 | Marlin |
| 9,451,999 | B2 | 9/2016 | Simpson et al. |
| 9,668,781 | B2 * | 6/2017 | Stark ................ A61B 17/7055 |
| 2002/0049447 | A1 | 4/2002 | Li |
| 2002/0198527 | A1 | 12/2002 | Muckter |
| 2004/0038179 | A1 | 2/2004 | Kumar et al. |
| 2006/0106382 | A1 | 5/2006 | Gournay et al. |
| 2006/0161154 | A1 | 7/2006 | McAfee |
| 2006/0161261 | A1 | 7/2006 | Brown et al. |
| 2007/0027543 | A1 | 2/2007 | Gimble et al. |
| 2007/0265621 | A1 | 11/2007 | Matthis et al. |
| 2007/0270879 | A1 | 11/2007 | Isaza et al. |
| 2008/0021454 | A1 | 1/2008 | Chao et al. |
| 2008/0021456 | A1 | 1/2008 | Gupta et al. |
| 2008/0039343 | A1 | 2/2008 | Abdou |
| 2008/0140082 | A1 | 6/2008 | Erdem et al. |
| 2009/0018660 | A1 | 1/2009 | Roush |
| 2009/0024174 | A1 | 1/2009 | Stark |
| 2009/0099610 | A1 | 4/2009 | Johnson et al. |
| 2009/0216238 | A1 | 8/2009 | Stark |
| 2009/0259261 | A1 | 10/2009 | Reiley |
| 2010/0010496 | A1 | 1/2010 | Isaza et al. |
| 2010/0042164 | A1 | 2/2010 | Lee et al. |
| 2010/0087878 | A1 | 4/2010 | Abdou |
| 2010/0094290 | A1 | 4/2010 | Vaidya |
| 2010/0106200 | A1 | 4/2010 | Stark |
| 2010/0131011 | A1 | 5/2010 | Stark |
| 2010/0298838 | A1 | 11/2010 | Walters |
| 2012/0095515 | A1 | 4/2012 | Hamilton |
| 2013/0004916 | A1 | 1/2013 | Bellanca et al. |
| 2013/0022942 | A1 | 1/2013 | Zadeh |
| 2013/0090696 | A1 | 4/2013 | Chiquillo Perez |
| 2013/0144344 | A1 | 6/2013 | Giancola |
| 2014/0012340 | A1 * | 1/2014 | Beck ................ A61B 17/8645 606/86 R |
| 2014/0046381 | A1 | 2/2014 | Asfora |
| 2014/0100616 | A1 | 4/2014 | Shipp |
| 2014/0222087 | A1 | 8/2014 | Greenberg et al. |
| 2014/0257408 | A1 | 9/2014 | Trieu et al. |
| 2014/0303676 | A1 | 10/2014 | Stroncek et al. |
| 2015/0233305 | A1 | 3/2015 | Meade et al. |
| 2015/0105833 | A1 | 4/2015 | Simpson et al. |
| 2015/0182309 | A1 | 7/2015 | Soler et al. |
| 2016/0015483 | A1 | 1/2016 | Kumar et al. |
| 2016/0120627 | A1 | 5/2016 | Gil Mur et al. |
| 2016/0262819 | A1 | 9/2016 | May et al. |
| 2016/0310188 | A1 | 10/2016 | Marino et al. |
| 2017/0224393 | A1 * | 8/2017 | Lavigne ............ A61B 17/7098 |

* cited by examiner

SACRO-ILIAC JOINT IMPLANT SYSTEM AND METHOD

TECHNICAL FIELD

The present disclosure generally relates to medical devices for the treatment of musculoskeletal disorders, and more particularly to a surgical system and a method for treating a sacro-iliac joint.

BACKGROUND

The sacro-iliac joint is a diarthrodial joint that joins the sacrum to the ilium bones of the pelvis. In the sacro-iliac joint, the sacral surface has hyaline cartilage that moves against fibrocartilage of the iliac surface. The spinal column is configured so that the weight of an upper body rests on the sacro-iliac joints at the juncture of the sacrum and ilia. Stress placed on the sacro-iliac joints in an upright position of the body makes the lower back susceptible to injury.

Disorders of the sacro-iliac joint can cause low back and radiating buttock and leg pain in patients suffering from degeneration and laxity of the sacro-iliac joint. In some cases, the sacro-iliac joint can undergo dehydration and destabilization, similar to other cartilaginous joints, which causes significant pain. The sacro-iliac joint is also susceptible to trauma and degeneration, from fracture and instability. It is estimated that disorders of the sacro-iliac joint are a source of pain for millions of people suffering from back and radicular symptoms.

Non-surgical treatments, such as medication, injection, mobilization, rehabilitation and exercise can be effective, however, may fail to relieve the symptoms associated with these disorders. Surgical treatment of these disorders can include the use of implants for fusion and/or fixation to provide stability to a treated region. During surgical treatment, surgical instruments can be used to deliver the implants to a surgical site for fixation with bone to immobilize a joint. The present disclosure describes an improvement over these prior technologies.

SUMMARY

In one embodiment, a sacro-iliac implant is provided. The sacro-iliac implant includes a body having a proximal portion and a distal tip. The proximal portion includes an inner surface and a uniform diameter. The inner surface includes a first mating surface engageable with a first instrument surface and a second mating surface engageable with a second instrument surface. Systems, constructs, instruments and methods are disclosed.

In one embodiment, a sacro-iliac implant system is provided. The sacro-iliac implant system comprises a sacro-iliac implant including a proximal portion and a distal tip. The proximal portion includes an inner surface and a uniform diameter. The inner surface includes a connection interface surface and a torque interface surface. A surgical instrument includes a first surface engageable with the connection interface surface and a second surface engageable with the torque interface surface.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system and method for treating a sacro-iliac (SI) joint. In some embodiments, the surgical system and methods of use disclosed provide stability and maintain structural integrity while reducing stress on the SI joint. In some embodiments, the present disclosure may be employed to treat musculoskeletal disorders including SI dysfunction or syndrome, dehydration, destabilization and/or laxity.

In some embodiments, the surgical system of the present disclosure comprises an SI implant. In some embodiments, the SI implant includes a threaded body. In some embodiments, the SI implant is cannulated. In some embodiments, the SI implant includes a body that is fenestrated to enhance SI joint fusion and to provide fixation of large bones and large bone fragments of the pelvis. In some embodiments, the present system includes one or more spinal constructs having one or more SI implants that are provided having various lengths to accommodate patient anatomy. In some embodiments, the SI implant is utilized with an SI joint fusion procedure for conditions including SI joint disruptions and degenerative sacroiliitis.

In some embodiments, the SI implant includes a fully threaded body having a thread form that extends an entire length of the body from a proximal end to a tip of a distal end. In some embodiments, the SI implant is cannulated and fenestrated to allow for bony ingrowth and for bone graft material to be packed inside the SI implant and on or about one or more components of the spinal construct to promote fusion across the SI joint. In some embodiments, the SI implant includes a recess on a proximal end to facilitate a threaded engagement with a surgical instrument, such as, for example, an inserter. In some embodiments, the inserter is configured for manual insertion, assisted with navigation and/or with a powered driver.

In some embodiments, the present surgical system includes a tapered, fully threaded, cannulated, fenestrated SI implant for stabilization and fusion of the SI joint. In some embodiments, the present surgical system is employed with a method for treating low back pain attributed to the SI joint. In some embodiments, the present surgical system includes a threaded SI implant that is cannulated, fenestrated, and designed to enhance SI joint fusion and provide fixation of large bones and large bone fragments of the pelvis. In some embodiments, the SI implant includes a distal tip having a blunt configuration. In some embodiments, the SI implant includes a bore having a threaded portion. In some embodiments, the threaded portion is configured to facilitate a revision procedure. In some embodiments, the bore includes a connection portion and/or a torque portion.

In some embodiments, the present system is employed with a method used with surgical navigation, such as, for example, fluoroscope or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In some embodiments, the present system is employed with a method for treating an SI joint, which includes the step of identifying a posterior superior iliac spine on a patient that is positioned in a prone position on an operating table. In some embodiments, the step of identifying includes using the posterior superior iliac spine as a landmark for making an incision. In some embodiments, identification of the posterior superior iliac spine limits vascular and muscular disruption from a surgical approach. In some embodiments, the method includes the step of establishing a trajectory path using fluoroscopy and a guide wire inserted into the posterior superior iliac spine, for example, on an iliac side of an SI joint. In some embodiments, bone graft material, such as, for example, autograft and/or allograft is inserted into the SI joint space to create a bony contact between the iliac and sacrum sides. In some embodiments, the bone graft material is inserted into a cannula of a screw.

In some embodiments, the present system includes an SI fixation screw attached to a surgical driver. In some embodiments, the SI fixation screw is employed with a method for treating an SI joint, which includes the step of applying a downward force and driving the screw through the ilium, through the graft material and into the sacrum following a path created by a reamer until the screw is flush with the ilium and docked into the sacrum. In some embodiments, screw placement is confirmed with fluoroscopy and/or image guidance and the incision is closed.

In some embodiments, the present system is employed with a method for screw removal from the SI joint fusion. In some embodiments, the method includes the step of providing an implant inserter configured to attach to the screw. In some embodiments, the method includes the step of exposing an iliac side of the SI joint of a patient who underwent a SI fusion procedure. In some embodiments, a tube can be placed over the incision site. In some embodiments the dorsal aspect of the screw is positively identified. In some embodiments, the dorsal aspect of the screw is identified by fluoroscopy and/or image guidance. In some embodiments, the implant inserter is re-attached to the dorsal end of the screw and the screw is removed.

In some embodiments, the present system includes an SI implant and a surgical inserter that employs image guidance, for example, surgical navigation. In some embodiments, the present system includes an SI implant and a surgical inserter that selectively, precisely and/or accurately connects the SI implant with the surgical inserter such that the SI implant extends a selected distance from the surgical inserter in connection with surgical navigation. In some embodiments, the SI implant extends a selected distance from the surgical inserter within an accuracy and/or tolerance of ±1.0 millimeter (mm). In some embodiments, the SI implant extends a selected distance from the surgical inserter, and is connected at a first component interface having a selected distance within an accuracy and/or tolerance of ±0.5 mm. In some embodiments, the component interface has a selected distance within an accuracy and/or tolerance of ±0.2 mm. In some embodiments, the component interface includes a threaded pocket of the SI implant. In some embodiments, the surgical inserter includes a floating, relative rotating sleeve disposed along a shaft of a driver. In some embodiments, the sleeve comprises a portion of the component interface to selectively locate the SI implant at the end of the driver while allowing the driver to pass through the sleeve and engage a second component interface of the SI implant. In some embodiments, the SI implant extends a selected distance from and is fixed with the surgical inserter in connection with image guidance to provide position of the SI implant with tissue for a reliable explant strategy, which may include locating the SI implant with tissue and explant of the SI implant.

In some embodiments, one or all of the components of the system are disposable, peel-pack or pre-packed sterile devices. One or all of the components of the system may be reusable. The system may be configured as a kit with multiple sized and configured components.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, muscle, ligaments, tendons, cartilage and/or bone unless specifically referred to otherwise.

The following discussion includes a description of a surgical system including an SI implant, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of an SI implant system 10.

The components of SI implant system 10 can be fabricated from biologically acceptable materials suitable for medical applications, including metals, synthetic polymers, ceramics and bone material and/or their composites. For example, the components of SI implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of SI implant system 10 may have material composites, including the above materials, to achieve various desired characteristics such as strength, rigidity, elasticity, compliance, biomechanical performance, durability and radiolucency or imaging preference. The components of SI implant system 10, individually or collectively, may also be fabricated from a heterogeneous material such as a combination of two or more of the above-described materials. The components of SI implant system 10 may be monolithically formed, integrally connected or include fastening elements and/or instruments, as described herein.

SI implant system 10 includes an implant, such as, for example, an SI implant 12. SI implant 12 is configured for use with treatment of SI joint disorders, as described herein, and including those caused by degeneration or trauma. SI implant 12 includes a body 14. Body 14 defines an axis X1. In some embodiments, body 14 can be variously configured, such as, for example, oval, oblong, triangular, square, polygonal, irregular, uniform, non-uniform, variable, hollow and/or tapered. Body 14 includes a proximal portion, such as, for example, a shaft 16 and a distal tip 18.

Shaft 16 includes a cylindrical cross-section and extends between an end 52 and an end 54. Shaft 16 includes an inner surface 20 that defines a longitudinal cavity 22. In some embodiments, cavity 22 extends along axis X1. In some embodiments, cavity 22 may be disposed in various orientations, such as, for example, perpendicular, transverse and/or at angular orientations, such as acute or obtuse relative to axis X1. Cavity 22 extends through body 14 such that SI implant 12 includes a cannulated configuration. In some embodiments, cavity 22 extends through all or only a portion of shaft 16. In some embodiments, cavity 22 extends through all or only a portion of tip 18.

End 52 includes a proximal most end surface of shaft 16. The proximal most end surface includes a substantially flat profile and is disposed in a plane substantially perpendicular to axis X1. In some embodiments, the proximal most end surface may be disposed in various orientations, such as, for example, perpendicular, transverse and/or at angular orientations, such as acute or obtuse relative to axis X1. End 52 and surface 20 include a mating surface 32, which is threaded and disposed adjacent the proximal most end surface. In some embodiments, all or a portion of surface 32 is threaded. In some embodiments, end 52 defines a recess or pocket including surface 32.

Surface 32 comprises a portion of a connection interface with a surgical instrument, as described herein, to releasably fix SI implant 12 with the surgical instrument at a selected position to facilitate guidance, insertion and manipulation of SI implant 12 to a surgical site, as described herein. In some embodiments, surface 32 provides a threaded connection with a surgical instrument, as described herein, to fix SI implant 12 with the surgical instrument. In some embodiments, SI implant 12 is connected with a surgical instrument such that SI implant 12 extends a selected distance from the surgical instrument in connection with treatment using surgical navigation, as described herein.

Figure 1:
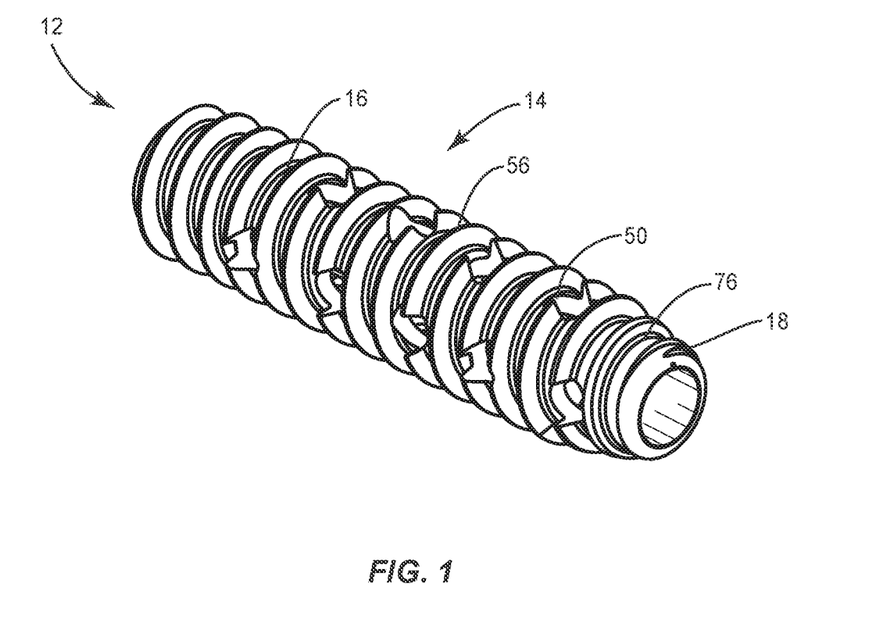
FIG. 1 is a perspective view of components of one embodiment of a system in accordance with the principles of the present disclosure.
Figure 2:
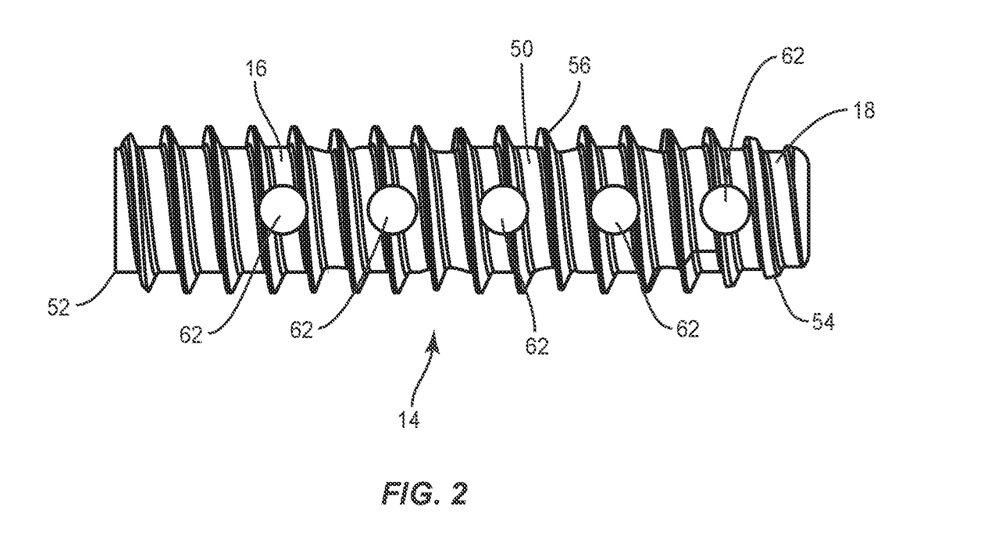
FIG. 2 is a side view of the components shown in FIG. 1.
Figure 3:
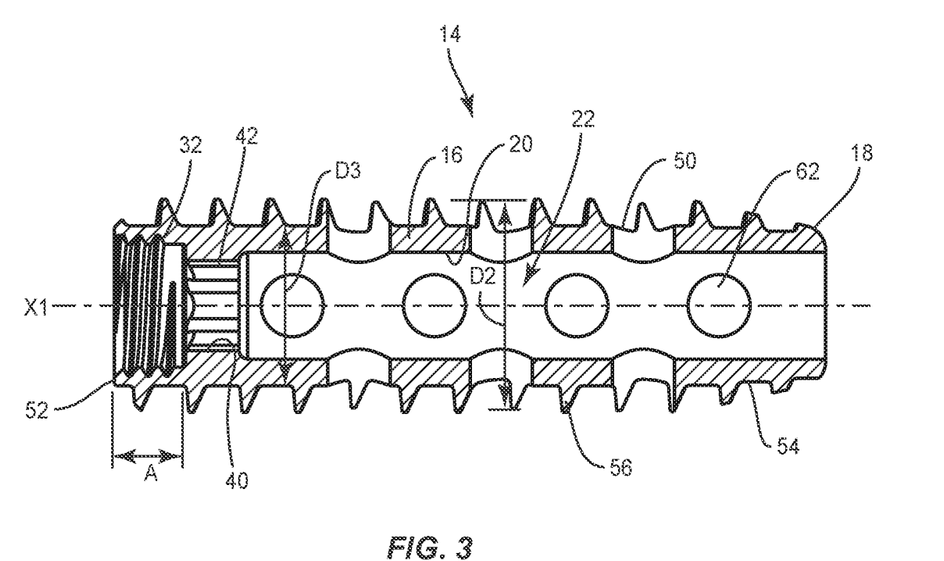
FIG. 3 is a cross section view of the components shown in FIG. 1.

Surface 32 extends a distance A measured from the proximal most end surface of shaft 16 into cavity 22, as shown in FIG. 3. In some embodiments, distance A is selected to connect SI implant 12 with a surgical instrument in connection with image guidance, as described herein, to dispose SI implant 12 relative to and/or extending from a surgical instrument, as described herein, and provide indicia of the position of SI implant 12 relative to the surgical instrument and/or tissue. In some embodiments, selected distance A effectively fixes SI implant 12 with a surgical instrument in connection with image guidance to provide position of SI implant 12 with tissue for a reliable explant strategy, which may include locating SI implant 12 with tissue and explant of SI implant 12. In some embodiments, distance A can be selected in a range of 2 through 8 mm. In some embodiments, selected distance A is 4 mm. In some embodiments, surface 32 extends a selected distance A within an accuracy and/or tolerance of ±0.5 mm. In some embodiments, surface 32 extends a selected distance A within an accuracy and/or tolerance of ±0.2 mm.

End 52 and surface 20 include a mating surface that defines a socket 42. Socket 42 is connected and/or directly adjacent with surface 32. In some embodiments, socket 42 may be spaced apart and disposed adjacent to surface 32. Socket 42 is disposed directly adjacent and distal to surface 32 such that socket 42 and surface 32 are co-axially disposed in a serial orientation along axis X1. In some embodiments, socket 42 and surface 32 may be disposed at alternate orientations relative to each other, such as, for example, proximal-distal, transverse, perpendicular, offset, non-concentric or staggered. In some embodiments, end 52 defines a recess or pocket including surface 32 and socket 42.

The surface of shaft 16 defining socket 42 is configured for engagement with a drive surface of a surgical instrument, as described herein. Socket 42 defines a hexalobular cross section for disposal and engagement of a correspondingly shaped portion of the drive surface. In some embodiments, socket 42 defines a cruciform, phillips, square, polygonal or star cross sectional configuration for disposal and engagement of a correspondingly shaped portion of the drive surface. In some embodiments, a close fitting engagement and/or interference fit is created between the surface of shaft 16 defining socket 42 and the drive surface of the surgical instrument. The surface of shaft 16 defining socket 42 comprises a portion of a torque interface with the drive surface, as described herein, to drive, rotate, torque, insert, implant or otherwise connect SI implant 12 with tissue, for example, the articular surfaces of an SI joint, sacrum and ilium, as described herein.

Figure 6:
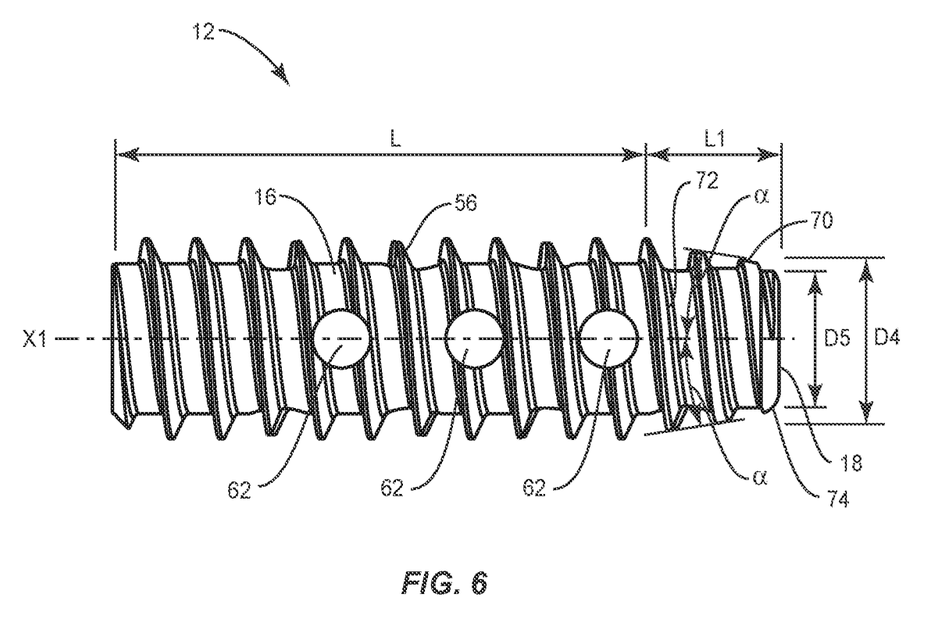
FIG. 6 is an enlarged view of the components shown in FIG. 2.

Shaft 16 includes an outer surface 50 that includes a thread 56. Thread 56 extends along a length L of shaft 16 between end 52 and end 54, as shown in FIG. 6. Thread 56 is continuous along surface 50. In some embodiments, thread 56 may be intermittent, staggered, discontinuous and/or may include a single thread turn or a plurality of discrete threads. In some embodiments, other penetrating elements may be located on shaft 16, such as, for example, a nail configuration, barbs, expanding elements, raised elements, ribs, and/or spikes to facilitate engagement of shaft 16 with tissue. In some embodiments, thread 56 may be self-tapping or intermittent. In some embodiments, length L is a distance selected from a range including 25 mm through 75 mm.

Figure 4:
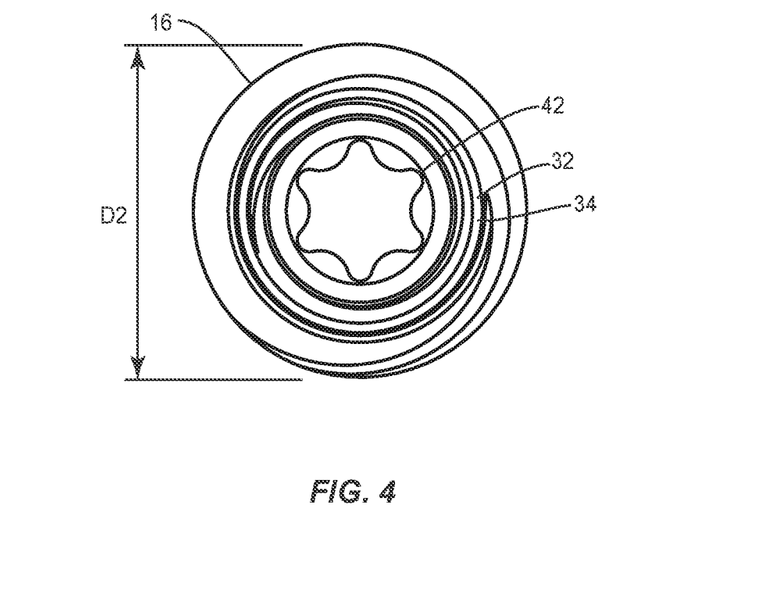
FIG. 4 is an end view of the components shown in FIG. 1.
Figure 5:
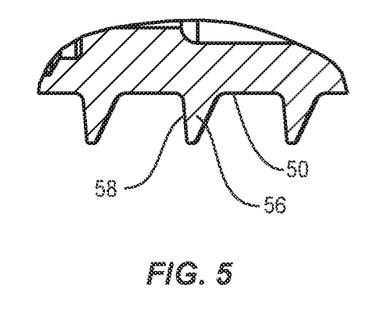
FIG. 5 is an enlarged break away view of the components shown in FIG. 3.

Thread 56 includes a major diameter D2 and a minor diameter D3, as shown in FIGS. 3 and 4. In some embodiments, diameter D2 and/or diameter D3 is uniform along length L. In some embodiments, a trailing edge 58 of thread form 56 is disposed perpendicular to surface 50 to resist and/or prevent back out of SI implant 12 from tissue. In some embodiments, a leading edge 60 of thread form 56 is disposed transverse to surface 50 to facilitate engagement of SI implant 12 with tissue. In some embodiments, thread 56 is trans-articular and penetrates tissue, including bone, of a sacrum to secure SI implant 12 with a sacro-iliac joint for stabilization and immobilization thereof. In some embodiments, all or only a portion of shaft 16 may have alternate surface configurations, for alternative fixation configurations with a body cavity, such as, for example, non-threaded, arcuate, undulating, substantially smooth, rough, spiked, semi-porous, dimpled and/or polished, textured for friction fit and/or oversized for pressure fit to facilitate fixation with tissue and/or include fastening elements such as anchors, barbs, spikes, detents and/or slots.

In some embodiments, shaft 16 includes a plurality of lateral openings, such as, for example, fenestrations 62. Fenestrations 62 extend between surfaces 20, 50 and are in communication with cavity 22. In some embodiments, fenestrations 62 allow the flow of an agent disposed within cavity 22 to promote bone growth adjacent a surgical site.

In some embodiments, the agent may include bone growth promoting material, such as, for example, bone graft to enhance fixation of SI implant 12 and/or other components of a spinal construct with tissue, as described herein. Osteogenic material may be included in the agent such as, for example, autologous bone harvested from the patient receiving the implant device, bone allograft, bone xenograft, any number of non-bone implants (for example ceramic, metallic, polymer), bone morphogenic protein, and/or bioresorbable compositions. For example, the osteogenic material may comprise minerals such as calcium phosphate or calcium sulfate minerals, bone, including xenograft, allograft or autograft bone. The osteogenic material may also comprise demineralized bone matrix (DBM), osteoinductive factors such as bone morphogenetic proteins (for example human BMP-2 or human BMP-7 or heterodimers thereof) whether recombinantly produced or purified from tissues, LIM mineralization proteins (LMPs), or the like. The osteogenic material may also comprise a binder material such as blood, clottable blood fractions, platelet gel, collagen, gelatin, carboxymethyl cellulose, or other similar materials that will serve to bind together harder particles or materials such as mineral particles (for example bone or synthetic mineral particles) to create a three-dimensionally stable mass when compacted into the cavities of SI implant 12 and/or other components of a spinal construct.

In some embodiments, the agent can contain other bioactive agents or other active agents, which may include one or a plurality of therapeutic agents and/or pharmacological agents for release, including sustained release, into an SI joint to treat, for example, pain, inflammation and degeneration. The agents may include pharmacological agents, such as, for example, antibiotics, pain medications, analgesics, anesthetics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

Tip 18 includes an outer surface 70 that extends between an end 72 and an end 74, as shown in FIG. 6. Surface 70 defines a profile that is disposed transverse to axis X1 forming a tapered configuration of tip 18. In some embodiments, surface 70 is disposed at an angle $\alpha$ in a range of 10 to 15 degrees relative to axis X1. End 72 defines diameter D4 and surface 70 tapers to a diameter D5 at end 74 to define the tapered profile of tip 18, which facilitates penetration of tissue. In some embodiments, tip 18 is tapered, for example, with a bevel for easier insertion and less tearing of the tissue, such as the cortical layers of the ilium and the sacrum. The distal most surface of tip 18 has a blunt configuration. In some embodiments, the distal most surface of tip 18 includes a sharpened point.

Surface 70 includes a thread 76 that extends along a length L1 of tip 18. Thread 76 is continuous along surface 70. In some embodiments, thread 76 may be intermittent, staggered, discontinuous and/or may include a single thread turn or a plurality of discrete threads. In some embodiments, other penetrating elements may be located on tip 18, such as, for example, a nail configuration, barbs, expanding elements, raised elements, ribs, and/or spikes to facilitate engagement of tip 18 with tissue. In some embodiments, thread 76 may be self-tapping or intermittent. In some embodiments, thread 56 includes a first thread form and thread 76 includes a second thread form, which may be the same or different than thread 56. In some embodiments, thread 76 may include a different pitch, diameter and/or crest shape than thread 56. In some embodiments, thread 76 is integral with thread 76.

Figure 7:
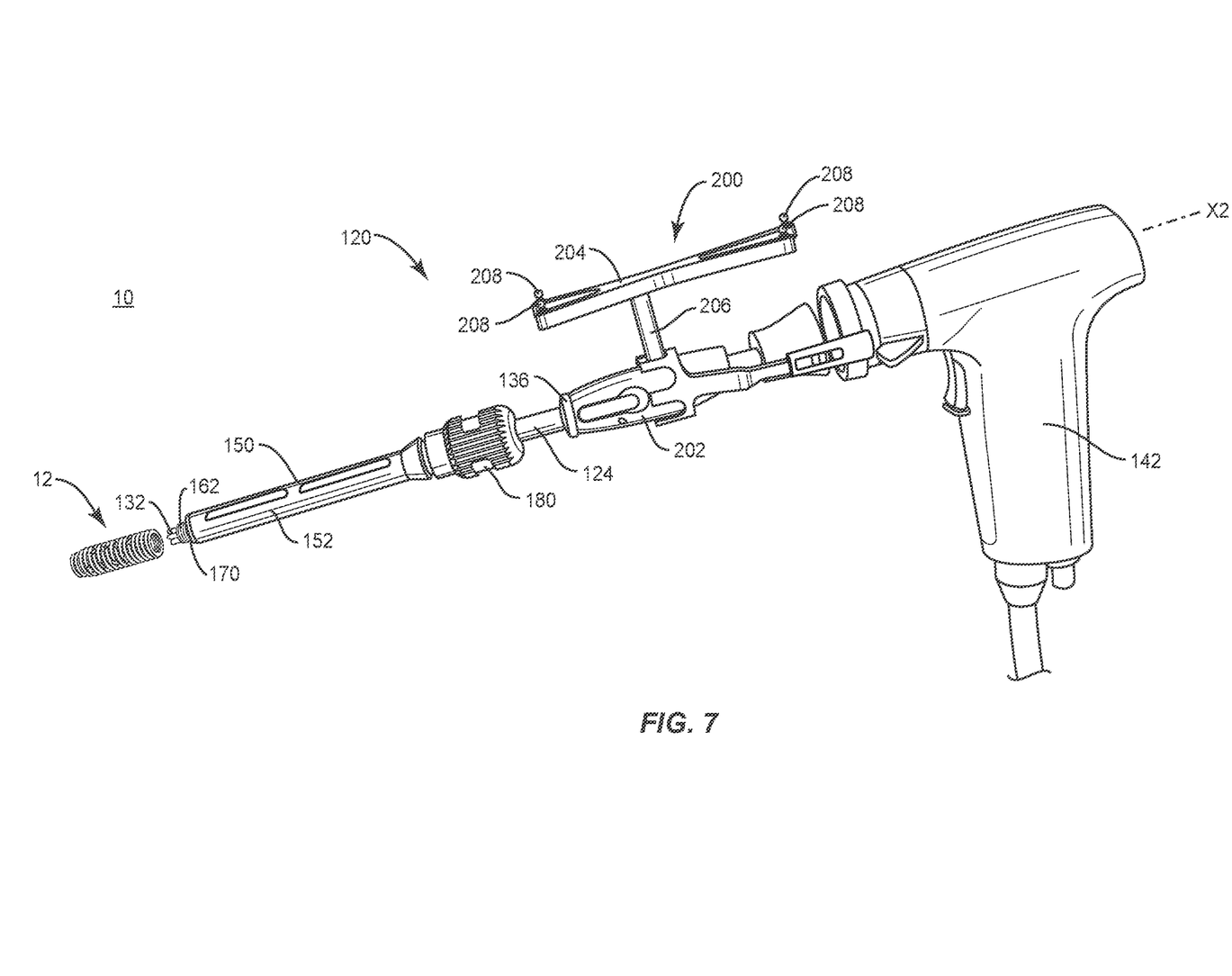
FIG. 7 is a perspective view of components of one embodiment of a system in accordance with the principles of the present disclosure.
Figure 8:
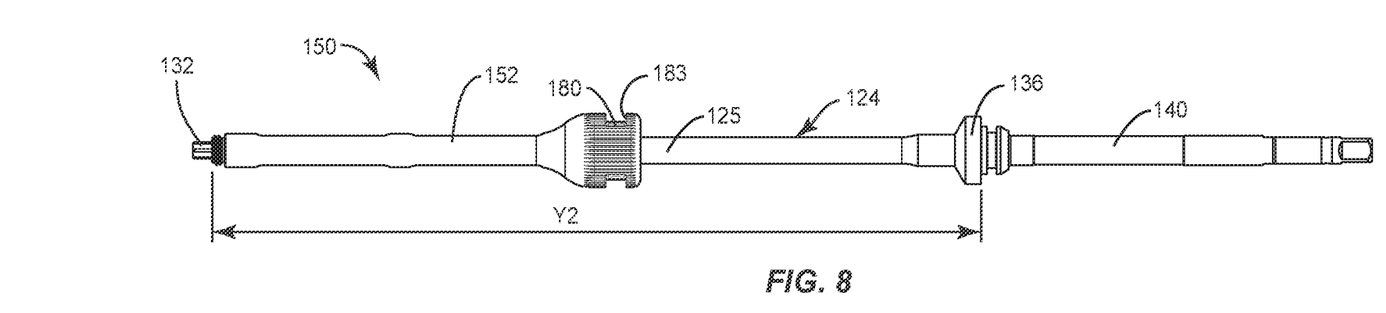
FIG. 8 is a side view of components of one embodiment of a system in accordance with the principles of the present disclosure.
Figure 9:
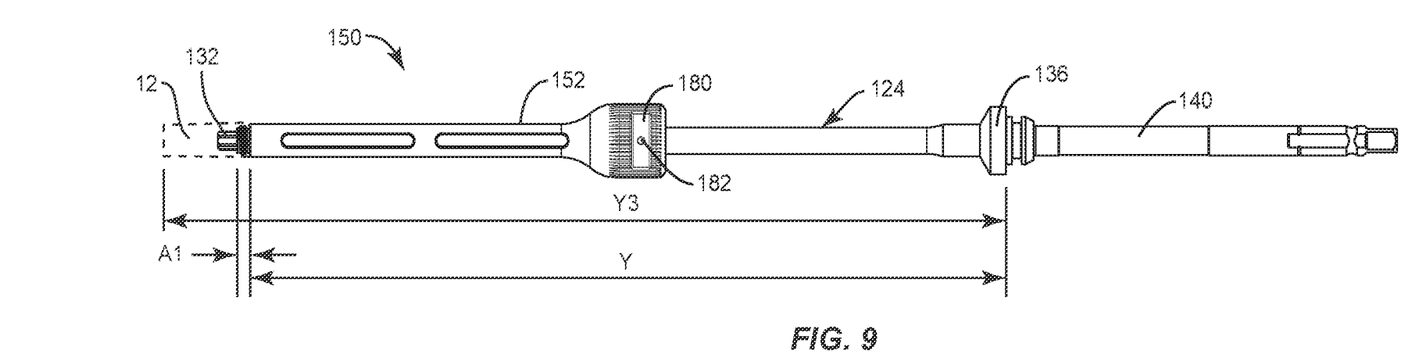
FIG. 9 is a side view of components of one embodiment of a system in accordance with the principles of the present disclosure.
Figure 10:
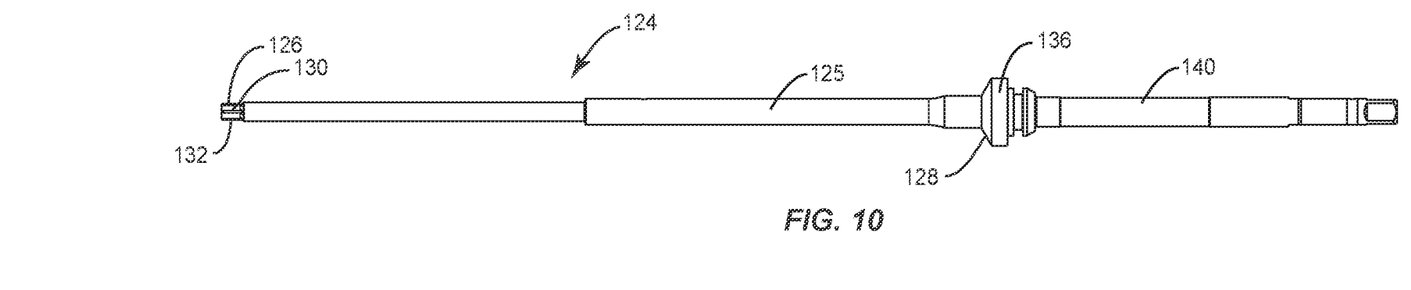
FIG. 10 is a side view of components of one embodiment of a system in accordance with the principles of the present disclosure.
Figure 11:
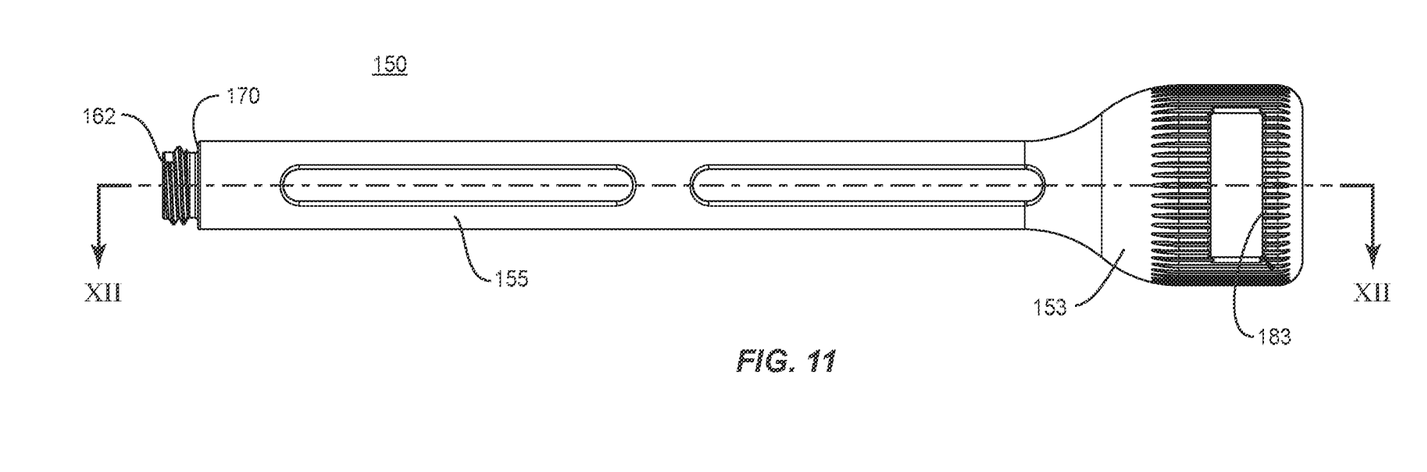
FIG. 11 is a side view of components of one embodiment of a system in accordance with the principles of the present disclosure.
Figure 12:
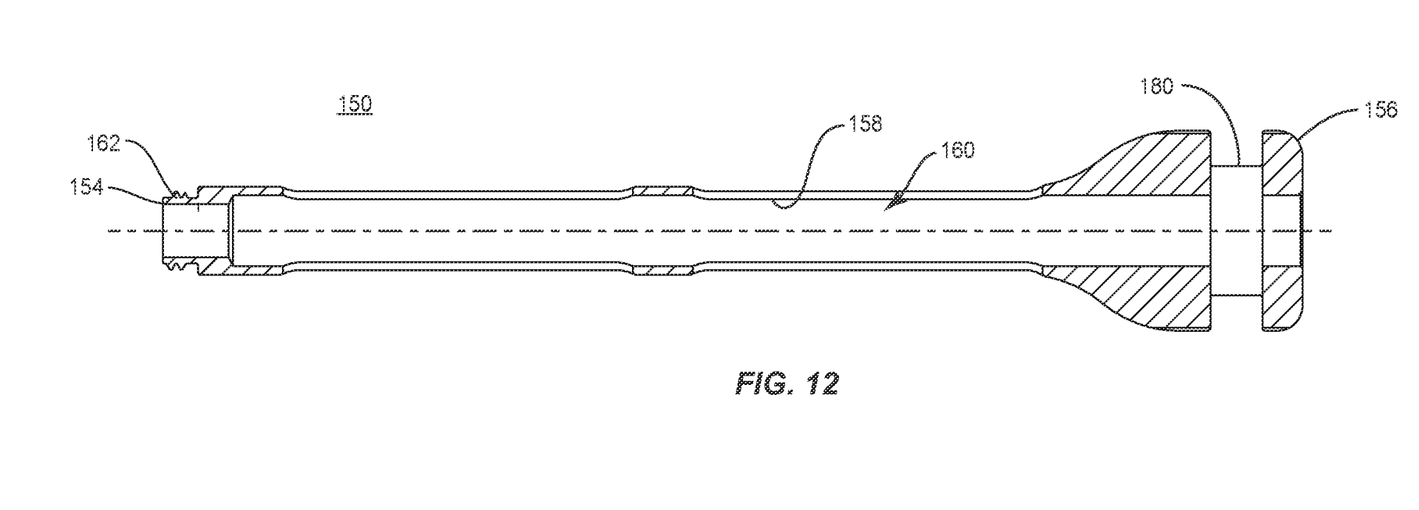
FIG. 12 is a cross section view of the components shown in FIG. 11.
Figure 13:
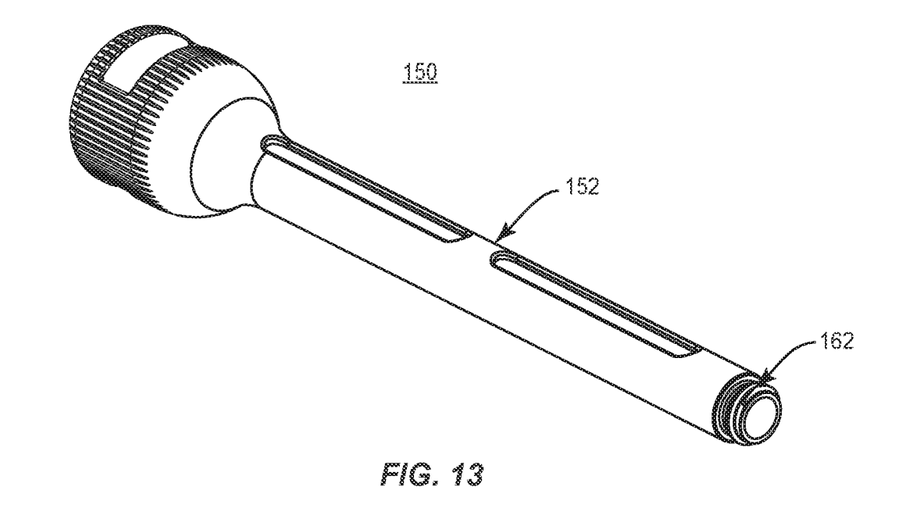
FIG. 13 is a perspective view of the components shown in FIG. 11.
Figure 14:
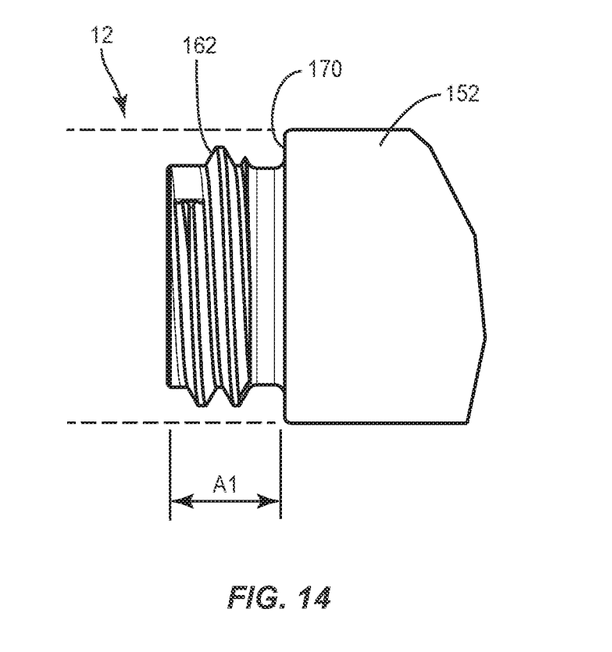
FIG. 14 is an enlarged break away view of the components shown in FIG. 11.

In assembly, operation and use, SI implant system 10, similar to the systems and methods described herein, is employed with a surgical procedure for treatment of an SI joint of a patient. SI implant system 10 may also be employed with other surgical procedures. In some embodiments, SI implant system 10 comprises a kit including a plurality of SI implants 12 of varying configuration and/or dimension, as described herein. In some embodiments, SI implant 12 is selected from the kit for employing with a treatment at the surgical site. SI implant 12 is connected with a surgical instrument 120 to facilitate insertion and manipulation of SI implant 12 utilizing an image guide, such as, for example, a navigation component 200, as shown in FIG. 7, of a medical imaging and navigation system (not shown), as described herein.

Surgical instrument 120 includes a driver 124, as shown in FIGS. 7-10. Driver 124 includes a shaft 125 that extends between an end 126 and an end 128. Driver 124 defines a longitudinal axis X1. In some embodiments, all or a portion of shaft 125 may have alternate cross section configurations, such as, for example, circular, oval, oblong, triangular, square, hexagonal, polygonal, irregular, uniform, non-uniform and/or tapered. In some embodiments, surgical instrument 120 may comprise and/or is connected with a tap, drill or a screwdriver.

End 126 includes a mating surface 130 having a hexalobular drive 132. Drive 132 is engageable with the surface of shaft 16 defining socket 42. Drive 132 includes a distal most surface of end 126. In some embodiments, drive 132 contacts the surface of socket 42 in a close fitting engagement and/or interference fit. Drive 132 comprises a portion of a torque interface with the surface of socket 42 to drive, rotate, torque, insert, implant or otherwise connect SI implant 12 with the articular surfaces of an SI joint and adjacent bone of the ilium and sacrum. In some embodiments, drive 132 may include a square, triangular, polygonal, star or torx cross section configured to engage the surface of socket 42.

End 128 includes a circumferential flange 136 disposed with shaft 125 at a position adjacent end 128 for connection with navigation component 200 at a selected position along shaft 125 to facilitate guidance, insertion and manipulation of SI implant 12 to a surgical site, as described herein. In some embodiments, flange 136 can be disposed at other various positions along driver 124. Flange 136 includes a proximal most surface and is configured to facilitate assembly with navigation component 200. Flange 136 is employed for a selected distance of components of SI implant system 10 from navigation component 200 in connection with a treatment using the surgical navigation system, as described herein. An adaptor 140 is engageable with shaft 125 to facilitate releasable engagement with an actuator 142, such as, for example, a powered drill, hand drill or other tool.

Surgical instrument 120 includes an inserter 150, as shown in FIGS. 8-14, to facilitate insertion and manipulation of SI implant 12 for delivery to a surgical site. Inserter 150 includes a sleeve 152. Sleeve 152 extends between an end 154 and an end 156. End 154 includes a shoulder 170 that defines a distal facing surface.

Sleeve 152 includes a housing 153 that is attached with a collar 180. Collar 180 is fixed with shaft 125 via a pin 182 to connect sleeve 152 with driver 124. Collar 180 is fixed along axis X1 and extends into openings 183 of housing 153 to capture sleeve 152 with shaft 125 and fix axial position of sleeve 152 along axis X1 to facilitate guidance, insertion and manipulation of SI implant 12 to a surgical site, as described herein. Sleeve 152 is rotatable about axis X1 relative to driver 124. For example, as shaft 125 is rotated to torque drive 132, as described herein, sleeve 152 can be held manually to resist and/or prevent rotation of sleeve 152. As such, sleeve 152 is fixed and shaft 125 is rotated such that collar 180 rotates through openings 183 and relative to housing 153. In another example, shaft 125 can be fixed and sleeve 152 manually rotated relative to driver 124 such that openings 183 rotate about collar 180, for example, to connect or release sleeve 152 from SI implant 12, as described herein. Sleeve 152 includes a shaft 155 that includes a surface 158. Surface 158 defines a passageway 160 configured for disposal and relative rotation of driver 124 therein.

Sleeve 152 is connected with shaft 125 such that SI implant 12 extends a selected distance from surgical instrument 120 in connection with treatment using surgical navigation, as described herein. The distal facing surface of shoulder 170 extends a distance Y measured from the proximal most surface of flange 136. In some embodiments, distance Y is selected to connect sleeve 152 with driver 124 in connection with navigation component 200 to dispose SI implant 12 relative to and/or extending from surgical instrument 120 and provide indicia of the position of SI implant 12 relative to the surgical instrument 120 and/or tissue. In some embodiments, distance Y can be selected in a range of 175 through 225 mm. In some embodiments, selected distance Y is 201 mm. In some embodiments, distance Y extends a selected distance within an accuracy and/or tolerance of ±0.25 mm. In some embodiments, distance Y extends a selected distance within an accuracy and/or tolerance of ±0.12 mm.

The distal facing surface of shoulder 170 includes a substantially flat profile and is disposed in a plane substantially perpendicular to axis X1. In some embodiments, the distal facing surface of shoulder 170 may be disposed in various orientations, such as, for example, perpendicular, transverse and/or at angular orientations, such as acute or obtuse relative to axis X1. End 152 includes a mating surface, such as, for example, a threaded surface 162. In some embodiments, all or a portion of surface 162 is threaded. Surface 162 comprises a portion of a connection interface with surface 32 to releasably fix SI implant 12 with surgical instrument 120 at a selected position relative to navigation component 200 to facilitate guidance, insertion and manipulation of SI implant 12 to a surgical site, as described herein.

Surface 162 extends a distance A1 from the distal facing surface of shoulder 170. In some embodiments, distance A1 is selected to connect SI implant 12 with surgical instrument 120 to dispose SI implant 12 relative to and/or extending from sleeve 152 and/or driver 124, and provide indicia of the position of SI implant 12 relative to surgical instrument 120 and/or tissue. In some embodiments, distance A1 can be selected in a range of 2 through 8 mm. In some embodiments, selected distance A1 is 3.5 mm. In some embodiments, surface 162 extends a selected distance A1 within an accuracy and/or tolerance of ±0.5 mm. In some embodiments, surface 162 extends a selected distance A1 within an accuracy and/or tolerance of ±0.2 mm. In some embodiments, distance A1 is equal to distance A. Surface 162 is connected with surface 32 such that SI implant 12 extends a selected distance from surgical instrument 120 and navigation component 200, as described herein.

Surgical Instrument 120 includes an image guide, such as, for example, navigation component 200, as described herein. Navigation component 200 is configured to generate a signal representative of a position of surgical instrument 120 and SI implant 12 to the navigation system. In some embodiments, the image guide may include one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 200 includes a housing 202 configured for disposal with shaft 125. Housing 202 is rotatable relative to shaft 125 about axis A1. In some embodiments, housing 202 is axially fixed with shaft 125 such that housing 202 is connected with shaft 125 and axial translation of housing 202 relative to shaft 125 is resisted and/or prevented.

Navigation component 200 includes a tracking device having an emitter array 204 that extends from and is connected to housing 202 via a post 206. Emitter array 204 is rotatable with housing 202 relative to shaft 125 about axis A1. In some embodiments, emitter array 204 is axially fixed with shaft 125 such that axial translation of emitter array 204 relative to shaft 125 is resisted and/or prevented. In some embodiments, emitter array 204 may be adjusted in rotation and/or an axial direction. In some embodiments, emitter array 204 may be disposed at alternate orientations relative to axis A1, such as, for example, parallel, perpendicular, transverse and/or other angular orientations, such as, acute or obtuse.

Emitter array 204 is configured for generating a signal representing a spatial position and/or a trajectory of surgical instrument 120 and SI implant 12 relative to a portion of a patient's anatomy and/or a depth of an SI implant within the patient's anatomy. Emitter array 204 includes four spaced apart arms having a substantially X-shape. Emitter array 204 includes markers, such as, for example fiducials 208. Fiducials 208 appear in an image produced by a surgical navigation system (not shown) for use as a point of reference or a measure. Emitter array 204 generates signals representing the position of various body reference points of the patient's anatomy.

Surgical instrument 120 is configured for disposal adjacent a surgical site such that navigation component 200 is oriented relative to a sensor array of a surgical navigation system. Orientation of navigation component 200 relative to the sensor array facilitates communication between navigation component 200 and the sensor array during a surgical procedure, as described herein. The sensor array receives signals from emitter array 204 to provide information regarding the spatial position and/or trajectory of surgical instrument 120 and SI implant 12 relative to a portion of the patient's anatomy, as described herein. See, for example, similar surgical navigation components and their use as described in U.S. Pat. Nos. 6,021,343, 6,725,080, 6,796,988, the entire contents of each of these references being incorporated by reference herein. In some embodiments, navigation component 200 includes at least one light emitting diode. In some embodiments, navigation component 200 may include other tracking devices capable of being tracked by the sensor array, such as, for example, a tracking device that actively generates acoustic signals, magnetic signals, electromagnetic signals, radiologic signals.

The surgical navigation system is configured for acquiring and displaying medical imaging, such as, for example, x-ray images appropriate for a given surgical procedure. In some embodiments, pre-acquired images of a patient are collected. In some embodiments, the surgical navigation system can include an O-arm® imaging device sold by Medtronic Navigation, Inc. having a place of business in Louisville, Colo., USA. An imaging device may have a generally annular gantry housing that encloses an image capturing portion.

In some embodiments, the image capturing portion may include an x-ray source or emission portion and an x-ray receiving or image receiving portion located generally or as practically possible 180 degrees from each other and mounted on a rotor relative to a track of the image capturing portion. The image capturing portion can be operable to rotate 360 degrees during image acquisition. The image capturing portion may rotate around a central point or axis, allowing image data of the patient to be acquired from multiple directions or in multiple planes. The surgical navigation system can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, the surgical navigation system can include C-arm fluoroscopic imaging systems, which can generate three-dimensional views of a patient. The position of the image capturing portion can be precisely known relative to any other portion of the imaging device. In some embodiments, a precise knowledge of the position of the image capturing portion can be used in conjunction with a tracking system to determine the position of the image capturing portion and the image data relative to the patient.

The tracking system can include various portions that are associated or included with the surgical navigation system. In some embodiments, the tracking system can also include a plurality of types of tracking systems, such as, for example, an optical tracking system that includes an optical localizer, such as, for example, a sensor array and/or an EM tracking system that can include an EM localizer. Various tracking devices can be tracked with the tracking system and the information can be used by the surgical navigation system to allow for a display of a position of an item, such as, for example, a patient tracking device, an imaging device tracking device, and an instrument tracking device, such as, for example, navigation component 200, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer where they may be forwarded to a surgical navigation computer. Image transfer may be performed over a standard video connection or a digital link including wired and wireless. The computer provides the ability to display, via a monitor, as well as save, digitally manipulate, or print a hard copy of the received images. In some embodiments, images may also be displayed to the surgeon through a heads-up display.

In some embodiments, the surgical navigation system provides for real-time tracking of surgical instrument 120 and SI implant 12. The sensor array is located in such a manner to provide a clear line of sight with emitter array 204, as described herein. In some embodiments, emitter array 204 communicates with the sensor array via infrared technology. The sensor array is coupled to the computer, which may be programmed with software modules that analyze signals transmitted by the sensor array to determine the position of each object in a detector space. A processor sends the information to the monitor, which provides a visual representation of the position of surgical instrument 120 and SI implant 12 relative to the patient's anatomy to allow the medical practitioner to move surgical instrument 120 and SI implant 12 to a desired location within the patient's anatomy.

In some embodiments, the patient tracking device provides a reference frame. The reference frame may be securely attached to the anatomy in the region of the body which is to receive the implant. By sensing the patient tracking device, the computer can determine the position of the anatomy in the detector space. The sensor array receives and triangulates signals generated by emitter array 204 to identify the relative position of each of the reference points and surgical instrument 120 and SI implant 12. The processor and the computer modify the image data set according to the identified relative position of each of the reference points during the procedure. The position and trajectory of surgical instrument 120 and SI implant 12 provided by emitter array 204 are processed by the processor and the computer, and are visually displayed against the preoperative image data set stored in the computer to provide the medical practitioner with a visual representation of the position, path and/or trajectory and depth of surgical instrument 120 and SI implant 12 relative to a portion of the patient's anatomy.

Figure 15:
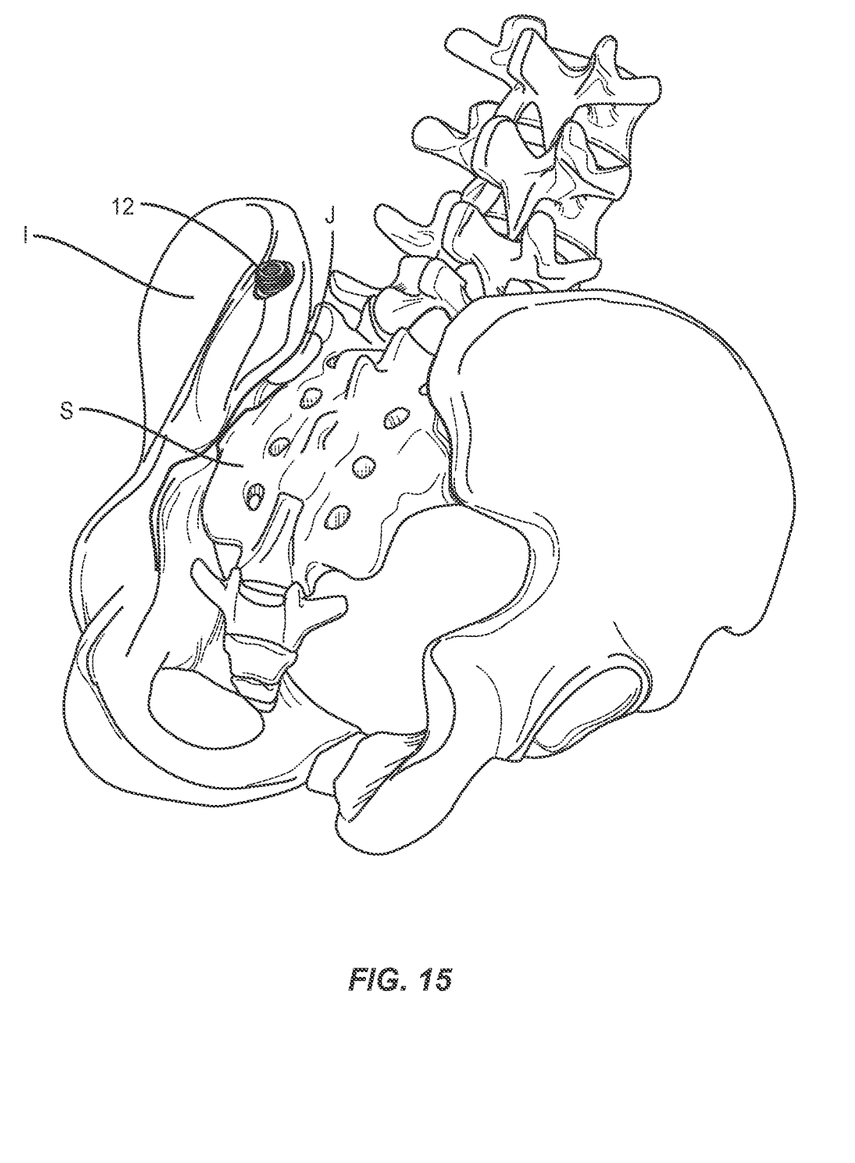
FIG. 15 is a perspective view of components of one embodiment of a system in accordance with the principles of the present disclosure disposed with vertebrae.

For example, SI implant system 10 is employed with a surgical arthrodesis procedure, such as, for example, fusion for treatment of an applicable condition or injury of an affected SI joint J, as shown in FIG. 15. SI implant 12 is connected with surgical instrument 120 to facilitate insertion and manipulation of SI implant 12 utilizing navigation component 200 and the navigation system, as described herein. In some embodiments, components of SI implant system 10 are inserted with SI joint J to space apart articular joint surfaces, establish joint tension, provide support and maximize stabilization of sacro-iliac joint J. In some embodiments, the components of SI implant system 10 are inserted with SI joint J as a SI joint spacer to restore ligamentous tension, eliminate painful micro-motion, and/or separate and cushion opposing articulating surfaces that cause pain. In some embodiments, SI implant system 10 may maintain joint tension without promoting bone growth.

In use, to treat a selected section of SI joint J, the body of a patient is disposed in a prone position on a surface, such as, for example, a surgical table (not shown). A surgical pathway of a posterior superior iliac spine (PSIS) of the body is identified. In some embodiments, the PSIS is identified through manipulation or tactile feedback by touching the skin of the patient. In some embodiments, the PSIS is identified through medical imaging, such as, for example, x-ray and/or fluoroscopy. An incision is made in the body of a patient and a cutting instrument (not shown) creates a surgical pathway for implantation of components of SI implant system 10. A preparation instrument (not shown) can be employed to prepare tissue surfaces of SI joint J, as well as for aspiration and irrigation of a surgical region.

Sleeve 152 is attached with driver 124, as described herein, such that drive 132 is disposed directly adjacent with surface 162. As such, drive 132 is disposed directly adjacent and distal to surface 162 such that drive 132 and surface 162 are co-axially disposed in a serial orientation along axis X1. A distal facing surface of surface 162 extends a distance Y2 measured from the proximal most surface of flange 136 and navigation component 200 to dispose SI implant 12 relative to and/or extending from surgical instrument 120 for display from the navigation system, as described herein. In some embodiments, distance Y2 can be selected in a range of 175 through 225 mm. In some embodiments, selected distance Y2 is 204.5 mm. In some embodiments, distance Y2 extends a selected distance within an accuracy and/or tolerance of ±0.25 mm. In some embodiments, distance Y2 extends a selected distance within an accuracy and/or tolerance of ±0.12 mm.

SI implant 12 is engaged with surgical instrument 120. Sleeve 152 is manually rotated relative to shaft 125, as described herein, in a clockwise direction to engage surface 162 with surface 32 in a threaded connection interface, as described herein. SI implant 12 is connected with surgical instrument 120 such that sleeve 152 captures end 52 and drive 132 is disposed with surface 42. Surface 32 is threaded with surface 162 such that the distal facing surface of shoulder 170 abuts the proximal most surface of end 52 in a substantially flush engagement. As such, SI implant 12 extends a selected distance that can be reliably measured, as described herein, from the surgical instrument 120. SI implant 12 and surgical instrument 120 are connected at the connection interface at a selected distance, which is measured from the proximal most surface of flange 136 and navigation component 200 within an accuracy and/or tolerance, as described herein, for display from the navigation system, as described herein.

SI implant 12 is delivered along the surgical pathway with surgical instrument 120 for implantation of components of SI implant system 10 including SI implant 12. A distal most surface of distal tip 18 extends a distance Y3 measured from the proximal most surface of flange 136 and navigation component 200 to dispose SI implant 12 relative to and/or extending from surgical instrument 120. In some embodiments, distance Y3 can be selected in a range of 200 through 275 mm. In some embodiments, selected distance Y3 is 241 mm. In some embodiments, distance Y3 extends a selected distance within an accuracy and/or tolerance of ±0.25 mm. In some embodiments, distance Y3 extends a selected distance within an accuracy and/or tolerance of ±0.12 mm. This configuration provides indicia or display from the navigation system, as described herein, of components of SI implant system 10 including SI implant 12, surgical instrument 120 and their relative positions with the tissue surfaces of SI joint J in connection with a surgical treatment, as described herein.

Driver 124 is engaged with SI implant 12 such that portion 132 is engaged with socket 42, as described herein. SI implant 12 is manipulated to orient SI implant 12 with the tissue surfaces of SI joint J for implant therewith. Actuator 142 is actuated to transmit a torque from actuator 142 to driver 124 such that drive 132 comprises a portion of a torque interface with the surface of socket 42 to drive, rotate, torque, insert, implant or otherwise connect SI implant 12 with the articular surfaces of an SI joint and adjacent bone of the ilium and sacrum. In some embodiments, a range of torque generated by actuator 142 and transmitted to SI implant 12 is approximately in a range of 0 to 21 Newton-meters (Nm).

SI implant 12 is implanted at the surgical site and surgical instrument 120 is disengaged from SI implant 12. Sleeve 152 is manually rotated relative to shaft 125, as described herein, in a counter-clockwise direction to disengage the threaded connection interface of surfaces 32, 162. SI implant 12 is fastened with the tissue surfaces of SI joint J, and released from sleeve 152 such that sleeve 152 and driver 124 disengage SI implant 12. In some embodiments, the torque transmitted to disengage sleeve 152 from SI implant 12 is less than the torque transmitted to SI implant 12 to fasten SI implant 12 with the tissue surfaces of SI joint J. As such, sleeve 152 is rotatable, relative to shaft 125, to release SI implant 12 therefrom and resists and/or prevents rotation of SI implant 12, which avoids disturbance, tissue damage, loosening or interference of implant fixation. In some embodiments, the torque transmitted to engage and create the connection interface, as described herein, includes hand tightening, negligible torque more than zero and/or the torque transmitted to engage and create the torque interface, as described herein. In some embodiments, the torque transmitted to engage and create the connection interface is different, the same or less than the torque interface.

Upon completion of the procedure, the surgical instruments, assemblies and non-implanted components of SI implant system 10 are removed from the surgical site and the incision is closed. One or more of the components of SI implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of SI implant system 10. In some embodiments, SI implant 12 is guided to the surgical site via a guidewire, such as, for example, a K-wire (not shown) and/or without the use of an image guide, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A sacro-iliac implant comprising:
    a body including a proximal portion and a distal tip, an outer surface of the body including a thread having a trailing edge disposed perpendicular to the outer surface and a leading edge disposed transverse to the outer surface, the body having a maximum length defined by a distance from an end surface of the proximal portion to an end surface of the distal tip, the thread extending the maximum length such that the body is fully threaded, the body defining a longitudinal cavity and a plurality of lateral openings in communication therewith, the lateral openings extending through the thread, the distal tip comprising an aperture that is in communication with the longitudinal cavity,
    the proximal portion including an inner surface and a uniform diameter, and
    the inner surface including a first mating surface engageable with a first instrument surface and a second mating surface engageable with a second instrument surface, the first mating surface including a threaded inner surface of the proximal portion and the second mating surface defining a hexalobular cross section of the proximal portion, the second mating surface defining a hexalobular cavity positioned between the first mating surface and the distal tip,
    wherein the longitudinal cavity has a diameter from the aperture to the hexalobular cavity that is greater than a diameter of the hexalobular cavity.

2. A sacro-iliac implant as recited in claim 1, wherein the first mating surface engages the first instrument surface in a connection interface with a surgical inserter.

3. A sacro-iliac implant as recited in claim 1, wherein the threaded inner surface is disposed adjacent a proximal most position of the proximal portion.

4. A sacro-iliac implant as recited in claim 1, wherein the second mating surface engages the second instrument surface in a torque interface with a surgical driver.

5. A sacro-iliac implant as recited in claim 1, wherein the mating surfaces are disposed in a serial orientation.

6. A sacro-iliac implant as recited in claim 1, wherein the distal tip includes a tapered configuration.

7. A sacro-iliac implant as recited in claim 1, wherein the body defines a longitudinal axis and the distal tip includes an outer surface oriented at an angle in a range of 0 through 15 angular degrees relative to the axis.

8. A sacro-iliac implant as recited in claim 1, wherein the distal tip includes a blunt configuration.

9. A sacro-iliac implant as recited in claim 1, wherein the first mating surface defines a bore, the bore having a diameter that is greater than the diameter of the longitudinal cavity from the aperture to the hexalobular cavity.

10. A sacro-iliac implant as recited in claim 1, wherein the first mating surface is spaced apart from the second mating surface by a flange that extends perpendicular to the longitudinal cavity.

11. A sacro-iliac implant comprising:
    a body including a shaft and a distal tip,
    the shaft including an inner surface that defines a longitudinal cavity and an outer surface having a uniform diameter, the outer surface including a thread having a leading edge disposed transverse to the outer surface and a trailing edge disposed perpendicular to the outer surface from the outer surface to a crest of the thread, the body having a maximum length defined by a distance from an end surface of the shaft to an end surface of the distal tip, the thread extending the maximum length such that the body is fully threaded, the shaft defining a plurality of lateral openings in communication with the longitudinal cavity, the lateral openings extending through the thread, the distal tip comprising an aperture that is in communication with the longitudinal cavity, and
    the inner surface including a connection interface surface and a torque interface surface disposed in a serial orientation, the connection interface surface including a threaded portion of the inner surface and the torque interface surface defining a cavity having a hexalobular cross section, the torque interface surface being positioned between the threaded portion and the distal tip, wherein the longitudinal cavity has a diameter from the aperture to the hexalobular cavity defined by the torque interface surface that is greater than a diameter of the hexalobular cavity defined by the torque interface surface.

12. A sacro-iliac implant system comprising:
a sacro-iliac implant including a proximal portion and a distal tip, an outer surface of the proximal portion including a first thread having a trailing edge disposed perpendicular to the outer surface and a leading edge disposed transverse to the outer surface, the proximal portion defining a longitudinal cavity and a plurality of lateral openings in communication therewith, the lateral openings extending through the first thread, the distal tip comprising an aperture that is in communication with the longitudinal cavity, an outer surface of the distal portion comprising a second thread including a different pitch, diameter and/or crest shape than the first thread, the sacro-iliac implant having a maximum length defined by a distance from an end surface of the proximal portion to an end surface of the distal tip, the first thread being continuous with the second thread such that the first and second threads define a helical thread extending the maximum length and the sacro-iliac implant is fully threaded, the proximal portion including an inner surface and a uniform diameter, the inner surface including a connection interface surface and a torque interface surface, the connection interface surface including a threaded inner surface of the proximal portion and the torque interface surface defining a hexalobular cross section of the proximal portion, the torque interface surface defining a hexalobular cavity positioned between the connection interface surface and the distal tip; and a surgical instrument including a first surface engageable with the connection interface surface and a second surface engageable with the torque interface surface,
wherein the longitudinal cavity has a diameter from the aperture to the hexalobular cavity that is greater than a diameter of the hexalobular cavity.

13. A sacro-iliac implant system as recited in claim 12, wherein the surgical instrument includes an image guide being oriented relative to a sensor to communicate a signal representative of a position of the sacro-iliac implant.

14. A sacro-iliac implant system as recited in claim 12, wherein the sacro-iliac implant is cannulated for disposal of a guide wire connected with tissue.

15. A sacro-iliac implant system as recited in claim 12, wherein the interface surfaces include a threaded surface and define a hexalobular cross section of the proximal portion.

16. A sacro-iliac implant system as recited in claim 12, wherein the surfaces of the surgical instrument include a threaded surface and a hexalobular drive disposed in a serial orientation.

17. A sacro-iliac implant system as recited in claim 12, wherein the first surface includes a sleeve having a distal threaded surface and the second surface includes a drive.

18. A sacro-iliac implant system as recited in claim 12, further comprising bone graft.

19. A sacro-iliac implant system as recited in claim 12, wherein the surgical instrument comprises:
an inserter including a sleeve comprising opposite first and second ends, the second end comprising the first surface; and
a driver including a shaft rotatably disposed in the sleeve such that a first end of the shaft is proximal to the first end of the sleeve and an opposite second end of the shaft is distal to the second end of the sleeve, the second end of the shaft comprising the second surface.

20. A sacro-iliac implant system as recited in claim 19, wherein the first end of the sleeve comprises a housing that is attached with a collar, the collar extending into openings of the housing and being fixed with the shaft via a pin.

* * * * *